United States Patent [19]

Ijiri et al.

[11] Patent Number: 5,173,684
[45] Date of Patent: Dec. 22, 1992

[54] LOW MOLECULAR WEIGHT ORGANIC LIQUID SENSOR AND DETECTION SYSTEM USING SAME

[75] Inventors: Yasuo Ijiri, Amagasaki; Toshio Kudo; Yasuo Shiraiwa, both of Tokyo, all of Japan

[73] Assignees: Mitsubishi Cable Industries, Ltd., Amagasaki; Tokyo Tatsuno Co., Ltd., Tokyo, both of Japan

[21] Appl. No.: 578,700

[22] Filed: Sep. 7, 1990

[30] Foreign Application Priority Data

Sep. 8, 1989 [JP] Japan ............................ 1-234482
Sep. 8, 1989 [JP] Japan ............................ 1-234483

[51] Int. Cl.⁵ ............................................. G08B 21/00
[52] U.S. Cl. ..................................... 340/605; 340/603; 73/40; 200/61.04
[58] Field of Search ............... 340/604, 605, 620, 603; 73/40, 40.5 R; 200/61.04, 61.05, 61.08

[56] References Cited

U.S. PATENT DOCUMENTS 3,970,863 7/1976 Kishikawa et al. ............ 340/605 X
4,206,632 6/1980 Suzuki ................................ 73/40.5 R
4,563,674 1/1986 Kobayashi ...................... 340/605 X

FOREIGN PATENT DOCUMENTS 57-19380 4/1982 Japan .

*Primary Examiner*—Jin F. Ng
*Assistant Examiner*—Jeffery A. Hofsass
*Attorney, Agent, or Firm*—Varndell Legal Group

[57] ABSTRACT

The invention provides a sensor whose conductive sheet is composed of substantially non-cross-linked thermoplastic elastomer and conductive carbon. The conductive sheet has a maximum of 70 of Shore A-hardness. By virtue of the above structure, the sensor very sharply responds to electric resistance of the conductive sheet against presence of low molecular weight organic liquid such as gasoline and vapor thereof to quickly detect leaked organic liquid or vapor with extremely sharp sensitivity. Furthermore, the detection system of the invention using the above sensor has a simple circuit which precisely detects varied electric resistance of the conductive sheet. The detection system characteristically incorporates an alarm generator to instantly warn operators of the presence of leaked organic liquid such as gasoline and vapor thereof.

16 Claims, 3 Drawing Sheets

LOW MOLECULAR WEIGHT ORGANIC LIQUID SENSOR AND DETECTION SYSTEM USING SAME

BACKGROUND OF THE INVENTION

1. FIELD OF THE INVENTION

The present invention relates to a sensor for detecting presence of low-molecular weight organic liquid such as gasoline and vapor thereof, and a detection system using this sensor.

2. DESCRIPTION OF THE PRIOR ART

Gasoline shares part of low-molecular weight organic liquid products, which is mainly used for the fuel of internal combustion engines, in particular, gasoline is mostly used for the fuel of automobile engines today. Normally, drivers refuel their automobiles at gasoline service stations. As it well known, gasoline is highly volatile and inflammable, and thus, extreme care must be taken while handling gasoline. As a matter of course, all the gasoline service stations strictly prohibit lighting of fire in the service site.

Conventionally, gasoline service stations store gasoline in underground tanks. Gasoline is supplied to the gas tank of each automobile by applying a refueling machine. Service men must very carefully supply gasoline to the automobile tank from the refueling machine. Gasoline leaked out of the refueling machine is quite dangerous because of potential fire hazard. In addition to a critical danger caused by leakage of highly volatile liquid, vapor thereof leads to a possibility of explosion when vaporized liquid concentration exceeds explosive limits. Therefore, leakage of highly volatile liquid should always be under strict observation.

The same applies to those low-molecular weight organic liquid products other than gasoline. To solve those problems mentioned above, one of the preceding arts proposes a sensor for detecting leakage of a low molecular weight organic liquid product such as gasoline. The proposed sensor is provided with an electric conductive sheet made from cross-linked organic material mainly composed of natural rubber and/or ethylene-propylene (EP) rubber. The sensor also has terminals which are provided on both ends of the conductive sheet.

Current constantly flows through the conductive sheet. If either low molecular weight organic liquid such as gasoline or vaporized content adheres to the conductive sheet, the affected portion of the conductive sheet swells to cause increase of electric resistance of the conductive sheet, and as a result, current cannot easily flow through the conductive sheet. The proposed sensor electrically detects such state and in turn detect presence of leaked low molecular weight organic liquid.

Normally, a sensor of this type is installed inside of an internal pipe of a refueling machine. However, responsivity of electric resistance of the conductive sheet against low molecular weight organic liquid and vaporized content is not very high, electric resistance of the conductive sheets does not readily rise even when either liquid or vaporized content of a low molecular weight organic product adheres to the conductive sheet.

On the other hand, when a sensor provided with a water-repellent film is exposed to highly-humid atmosphere for a long time, water or moisture may eventually reach the conductive sheet. If water or moisture adheres to the conductive sheet through the water-repellent film, it not only prevents the conductive sheet from swelling by the effect of adhered liquid or vapor of a low molecular weight organic product, but it also causes the sensor itself to malfunction as a result of the increased contact resistance between terminals and the conductive sheet due to corrosion of terminals by electrolysis.

As is clear from the above description, the conventional sensor is not only poor in sensitivity against leakage of low molecular weight organic liquid or vapor, but it also lowers responding characteristic due to adhesion of water or moisture, and thus, it cannot precisely detect leaked organic liquid or vapor. Because of this disadvantage, such a conventional sensor mentioned above is actually rarely used.

As the situation stands now, no measure is taken to effectively prevent leakage of low molecular weight organic liquid such as gasoline and vapor thereof particularly in gasoline service stations today.

SUMMARY OF THE INVENTION

Therefore, the primary object of the invention is to provide a novel low molecular weight organic liquid sensor which is ideally suited for detecting presence of low molecular weight organic liquid such as gasoline and vapor thereof in the event of leakage from an internal pipe of a refueling machine in gasoline service stations or other storage installation in facilities handling low molecular weight organic liquid, and for preventing environment from being polluted by leakage thereof.

Another object of the invention is to provide a novel detection system using the sensor mentioned above.

The above objects can be achieved by providing a novel sensor composed of an electric conductive sheet made from the blend of substantially non-cross-linked thermoplastic elastomers and conductive carbon, wherein the conductive sheet has a maximum of 70 of Shore A-hardness. The detection system of the invention is composed of a sensor, an element which generates an electric signal in response to the increased electric resistance of the sensor, an alarm signal generator which is operated by this signal, and a DC power-supply source which supplies DC power to the electrical circuit comprised therein.

The sensor embodied by the invention has a very sharp swelling property and high responsivity to electric resistance against low molecular weight organic liquid such as gasoline or vapor thereof.

There is no specific limitation on the kind of thermoplastic elastomer. Examples of thermoplastic elastomer include stylene-ethylene-butadien-styrene copolymer (SEBS), styrene-ethylene-butadiene copolymer, polybutadiene elastomer, olefin elastomer, and so on.

Thermoplastic elastomer to be used for embodying the invention is characterized by not being cross-linked substantially. The term "not being cross-linked substantially" designates such a concept which includes the one which is partially cross-linked for materializing thermoplastic property. That is, substantially non-cross-linked thermoplastic elastomer of the invention encompasses both polymer not cross-linked at all and polymer partially cross-linked. The degree of cross-linking when the polymer is partially cross-linked, according to JIS C3005 and expressed by gel percentage measured at 50° C. extraction temperature against xylene, is 3 –50%, preferably 4 –40%, more preferably 5 –30%.

Although there is also no specific limitation on the kind of conductive carbon for embodying the invention, conductive carbon black having a minimum of 250 ml/100 g of DBP (dibutyl phthalate) oil content and a minimum of 500 m$^2$/g of surface area is particularly preferable, which is exemplified by "KETZEN BLACK" (product of Lion Co., Ltd., Japan), "VULCAN" XC-72 (a product of Cabot Inc., USA), "DENKA" Acetylene Black (a product of Denki Kagaku Kogyo K.K., Japan), etc.

The blend of thermoplastic elastomer and conductive carbon has a maximum of 70 of Shore A-hardness (hardness of elastomer), preferably a maximum of 65, more preferably a maximum of about 50. Regarding the blend ratio of thermoplastic elastomer and conductive carbon, it is suggested that 10 through 100 weight parts, preferably 12 through 90 weight parts, more preferably 15 through 80 weight parts of conductive carbon be blended with 100 parts of thermoplastic elastomer.

The sensor embodied by the invention detects the presence (mainly leakage) of low molecular weight organic liquid or vaporized content. Liquid here means those which stably remain in liquid condition under room temperature. It is favorable that such liquid has a maximum of 300 molecular weight, in particular, a maximum of 150 molecular weight, examples of which include alcohols such as methanol, ethanol, or the like, lubricants such as transformer oil, ketones such as methylethyl ketone or acetone, light oil, kerosene, gasoline, naphtha, ligroin, benzene, toluene, xylene, chlorinated solvent such as chloroform, and so on.

Normally, terminals of the sensor of the invention are secured to the conductive sheet with eyelets via washers before being connected to lead wires by soldering means. However, from the viewpoint at applicable field, the sensor is often installed in an environmental condition in which the sensor constantly exposes itself not only to low molecular weight organic liquid or vapor, but to water and aqueous vapor as well. Although it varies depending on the environmental condition in which the sensor is installed, the sensor may be obliged to expose itself to highly humid atmsophere for many months or years. In this case, if the sensor has water-repellent film, it can repel water. However, since aqueous vapor permeates the water-repellent film, the water-repellent film is totally useless in the long run as though the film were not provided for the sensor. When the sensor is present in extremely humid environment for a long time, dew is repeatedly generated on terminals by the effect of incoming and outgoing of aqueous vapor through the water-repellent film. This eventually results in the occurrence of corrosion and rust at the contact between the terminals and the conductive sheet. In other words, corrosion and rust are generated because of electrolytic phenomenon between the surfaces of the eyelet-secured terminals, washers, and the conductive sheet. As a result, contact resistance between the terminals and the conductive sheet increases, thereby causing increase of the resistance value of the sensor which leads to frequent occurrence of malfunction. To prevent this, it is essential for the system to perfectly provide water-proof effect for the terminals and surrounding portions. For this purpose, it is suggested, for example, that these portions by fully coated with (a) wax such as paraffin wax or microcrystalline wax, (b) resin that can be cured under normal temperature such as polyurethane resin, epoxy resin, or silicone resin, or (c) acrylic paint or urethane paint.

After completing water-proof treatment provided for the terminals and surrounding portions, sensing performance is not adversely affected generally even though water or aqueous vapor adheres to the conductive sheet other than the terminals and surrounding portions. However, it is preferable that water-proof effect be also provided for portions other than those provided with the water-proof effect mentioned above. To implement this, it is suggested, for example, that the whole surfaces of the conductive sheet including the terminals be covered with water-repellent film, or at least the sheet surface (facing the front of the sensor) sharing the detecting operation be also covered with water-repellent film. However, there is no specific limitation.

Said water-repellent film need be provided with water repellent effect concurrently with air permeable effect, and complete water-proof effect on terminals suffices for the purpose. To concurrently achieve water-repellent and air-permeable effects, it is suggested that such water repellent film has a minimum of $10^4$/cm$^2$ of fine holes, preferably a minimum of $10^5$/cm$^2$ of fine holes, and most preferably a minimum of $10^6$/cm$^2$ of fine holes. As examples of film material, mention may be made of polytetrafluoroethylene, polyethylene, polypropyrene, etc.. For example, "MICROTEX" (a product of NITTO DENKO K.K., Japan) or "BREATHLON" (a product of NITTO DENKO K.K.) may be used. "MICROTEX" has more than several hundred millions of extremely fine holes per square centimeter. "BREATHLON" has a minimum of $10^6$cm$^2$ of extremely fine holes and features distinct water proof and air permeability. Both of these water-repellent films are most suited for use.

Even when the above water-repellent film is provided, the sensor of the invention must be handled with care since the sensor of the invention is extremely thin. In order to install the sensor to the organic-liquid or vapor piping and the like more easily, reinforced structure may be provided for the sensor. For example, as shown in FIG. 2, a reinforcing layer may be provided inside of the water-repellent film or back of the sensor as shown in FIG. 4. As material for such reinforcing layer, ABS resin, polypropylene, polyvinyl chloride resin, polyallylate resin, etc. may be preferably used.

To provide convenience for installing the sensor to the liquid piping and the like, it is suggested to provide the sensor with magnet or magnetic layer. For example, thin-sheet magnet, or plastic magnet or magnetic layer composed of magnetic material like ferrite may also be set on the back of the sensor or to the back of the reinforcing layer if the reinforcing layer is set to the back of the sensor. The sensor provided with magnetic force can easily be set to the magnetic housing composed of iron and the like on the way of installing the sensor to the organic-liquid piping and the like.

Generally, a soft and thin conductive sheet is employed for the sensor, which results in poor handling property in manufacturing process. To improve the handling property, the conductive sheet itself may be reinforced. In addition to preferable air-permeable material suited for the reinforcement, such as woven fabric, non-woven fabric, paper, etc., polyethylene film, polypropylene film, polyester film, etc. may also be used. From the viewpoint of simplicity of reinforcing structure and convenience of manufacture, it is preferable that the reinforcing film be bonded to the sheet surface facing the back of the sensor. The conductive sheet may be reinforced concurrently with the reinforcement of the sensor itself. By combining both reinforcements of the conductive sheet and the sensor, the sensor will have more preferable structure.

When operating the sensor of the invention, the conductive sheet swells itself in response to the adhesion of low-molecular weight organic liquid or vaporized content to the conductive sheet. Along with said swelling, electric resistance of the conductive sheet increases. By sensing the increase of electric resistance on the part of the conductive sheet, leakage of low molecular weight organic liquid or vaporized content is detected.

In view of the functional operation of the sensor, the sensor embodied by the invention is ideally suited for use in gasoline service stations. Normally in a gasoline service station, accident rarely occurs as a result of leaked gasoline. Actually, vaporized gasoline is most dangerous. When vaporized content of highly volatile gasoline reaches or exceeds explosive limits, danger of explosion is imminent. Explosion occurs when there is 1.4% of vaporized concentration of gasoline in atmosphere at the lowest limit. Therefore, even when the vaporized concentration of gasoline is less than 1.4%, presence of this vaporized gasoline must securely be detected earlier in order to preserve safety. Some gasoline service stations usually handling gasoline allow vaporized gasoline content to reach 0.3%. However, locations where gasoline is not dealt are totally free from vaporized gasoline concentration and it is thus reasonable for the concerned to recognize that 0.3% of vaporized gasoline concentration is quite abnormal. Accordingly, it is essential for the concerned to properly set a specific detection sensitivity according to the sensor-installed locations, in order to detect vaporized gasoline concentration, not to mention of detection of leaked liquid gasoline.

This can easily and securely be materialized by differentiating the detected concentration of vaporized gasoline by operating circuits of a detection system using the sensor embodied by the invention. For example, it is preferable that the detection circuit start to operate itself as soon as the electric resistance value of the sensor shows more than 5 times the initial value in a gasoline service station where gasoline is constantly handled. In locations other than gasoline service stations, it is preferable that the detection circuit start to operate itself as soon as the electric resistance value of the sensor shows more than 3 times the initial value. Furthermore, it is most ideal to set a certain voltage as a reference voltage and to have the detection circuit start to operate itself as soon as the measured terminal voltage at the time the electric resistance value of the sensor exceeds said predetermined multiple, exceeds the reference voltage.

The detection system of the invention characteristically comprises a sensor, an element which generates an electric signal in response to the increased electric resistance of the sensor, an alarm-signal generator which is activated on receipt of this electric signal, and a DC power-supply source which supplies DC power to the electrical circuit comprised therein.

Of those circuit components, the element which generates an electric signal in response to the increased electric resistance value of the sensor is most important. To compose this element, it is preferable that a comparator widely used for composing a comparative amplifying circuit comparing the differential magnitude between the reference voltage and the measured terminal voltage be employed. Assuming that the positive-side voltage (reference voltage) delivered to the comparator is $V_c$ and the negative-side voltage (measured terminal voltage) delivered to the comparator is $V_s$, both are normally in the relationship of $V_s < V_c$ in a circuit using a comparator, and thus, no output signal is obtained from the comparator. However, when the electric resistance of the sensor increases, the relationship between both voltages inverts by way of $V_s \geq V_c$, thus generating outgoing signal. The signal output from the comparator is delivered to the alarm signal generator so that alarm signal can be generated to warn people in the site of leakage of low molecular weight organic liquid or vaporized content. As far as the alarm signal generator can easily identify the signal from the comparator, there is no restriction on the kind of alarm means. For example, an LED display, a red alarm lamp, etc. make up visual identifying means and alarm sound or buzzer make up audible identifying means. To prevent the system from malfunctioning itself, it is preferable that regulated DC power-supply source be used. However, available power-supply source is not specifically restricted.

DETAILED DESCRIPTION OF THE PREFERRED EMBODIMENTS

Referring now to the accompanying drawings, embodiments of the sensor and the detection system of the invention are described below.

Figure 1:
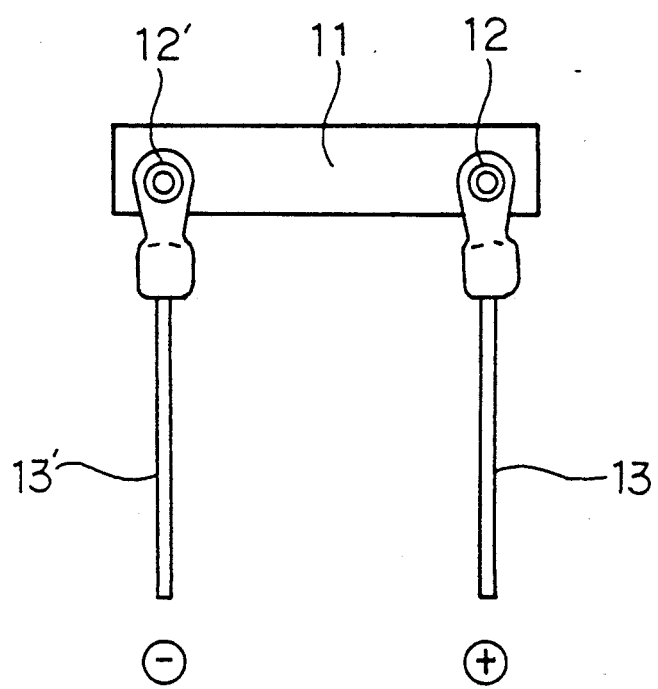
FIG. 1 is the plan designating an embodiment of the sensor related to the invention.

FIG. 1 illustrates an embodiment of the invention. A conductive sheet 11 sensing either low molecular weight organic liquid or vaporized content is composed of substantially non-cross-linked thermoplastic elastomer and conductive carbon mentioned earlier, where the conductive sheet 11 has a maximum of 70 of Shore A-hardness. Copper-lead terminals 12 and 12' are secured to both ends of the conductive sheet 11 by eyelet means. Lead wires 13 and 13' are respectively connected to these terminals 12 and 12'. Although not shown, as mentioned above, these terminals 12 and 12' and surrounding portions are provided with waterproof treatment.

The sensor related to the invention is installed inside of a refueling machine of a gasoline service station. More specifically, the sensor is installed inside of internal gasoline pipe where gasoline is likely to leak. The sensor causes DC current to constantly flow through the conductive sheet or causes it to flow through the conductive sheet only when measuring operation is performed. When liquid gasoline or vaporized content adheres to the conductive sheet 11 by leaking out of the internal pipe, the portion affected by adhered gasoline or vaporized content immediately starts to swell. As a result, electric resistance at the swollen portion increases to gradually intercept the flow of current. By electrically sensing the increased electric resistance according to the detection system described below, the sensor can warn people of the occurrence of leakage of gasoline or other low molecular weight organic liquid products.

Figure 2:
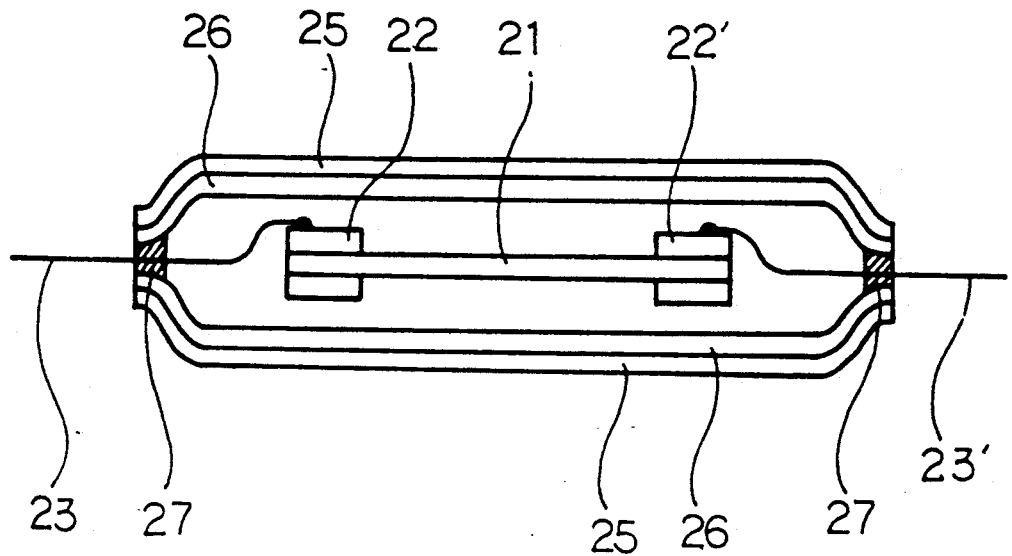
FIG. 2 is the vertical sectional view designating another embodiment of the sensor related to the invention.
Figure 3:
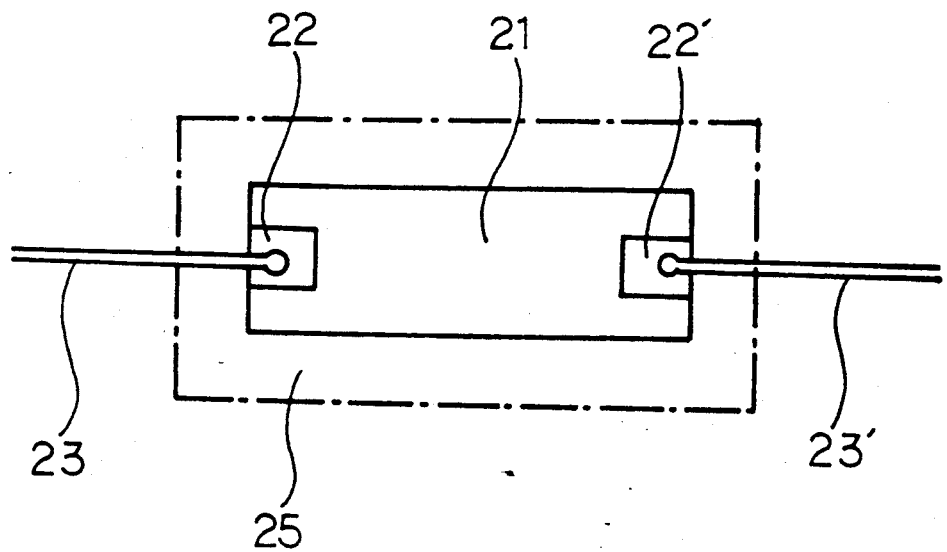
FIG. 3 is the plan of the sensor shown in FIG. 2.

FIGS. 2 and 3 respectively designate other embodiments. Copper-lead terminals 22 and 22' are secured to both ends of a conductive sheet 21 sensing low molecular weight organic liquid or vaporized content via eyelets. Lead wires 23 and 23' are respectively soldered to these terminals 22 and 22'. In the embodiments shown in FIGS. 2 and 3, "BREATHLON" (a product of NITTO DENKO K.K., porous polyethylene film) 25 is selected as the water-repellent film. A reinforcing polyester non-woven fabric 26 is bonded to the internal surface of the BREATHLON film 25 with adhesive agent. The bonded sheet fully covers the conductive sheet 11. Some portions of the non-woven fabric 26 in contact with the lead wires 23 and 23' are fully sealed by applying a thermally-melting adhesive agent 27. These terminals 22 and 22' and surrounding portion are also provided with water-proof treatment. In addition to water-proof provided for the terminals 22 and 22', the conductive sheet 21 is fully covered, and thus, the conductive sheet 21 is free from influence of water or moisture. Nevertheless, either organic liquid or vaporized content permeates the film 25 and the non-woven fabric 26 and then arrives at the conductive sheet 21.

Figure 4:
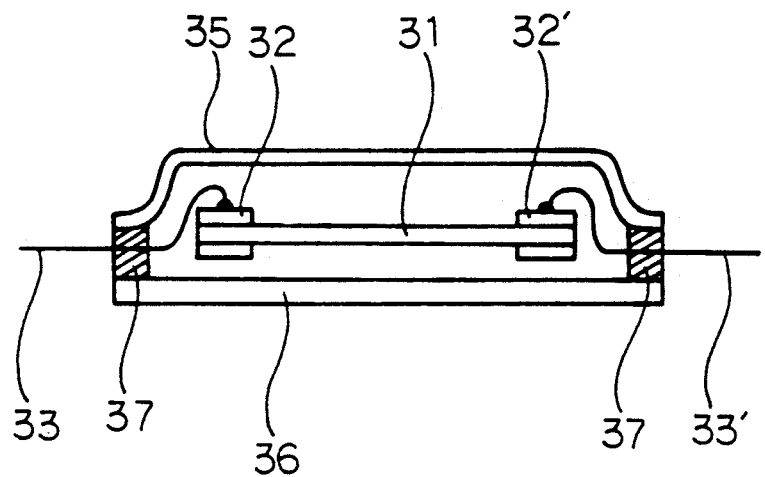
FIG. 4 is the vertical sectional view designating a still further aspect of the sensor embodied by the invention.

The sensor shown in FIG. 4 designates a modification of the sensor shown in FIG. 2. A porous polyethylene film 35 fully covers the front surface of the sensor, whereas the back surface thereof is covered with a reinforcing layer 36 to reinforce the entire structure of the sensor. By provision of the reinforcing layer 36, sensor handling convenience is promoted.

Magnetic layer (not shown) may also be provided on the back surface (externally exposed surface) of the reinforcing layer 36 for the sensor shown in FIG. 4. In this case, the sensor can be easily fixed to the magnetic housing by magnetic force. In addition, a sheet reinforcing layer can also be provided on the back surface (facing the reinforcing layer 36) of the conductive sheet 31. This facilitates handling of the conductive sheet 31 when processing this sheet into the sensor structure shown in FIG. 4.

Figure 5:
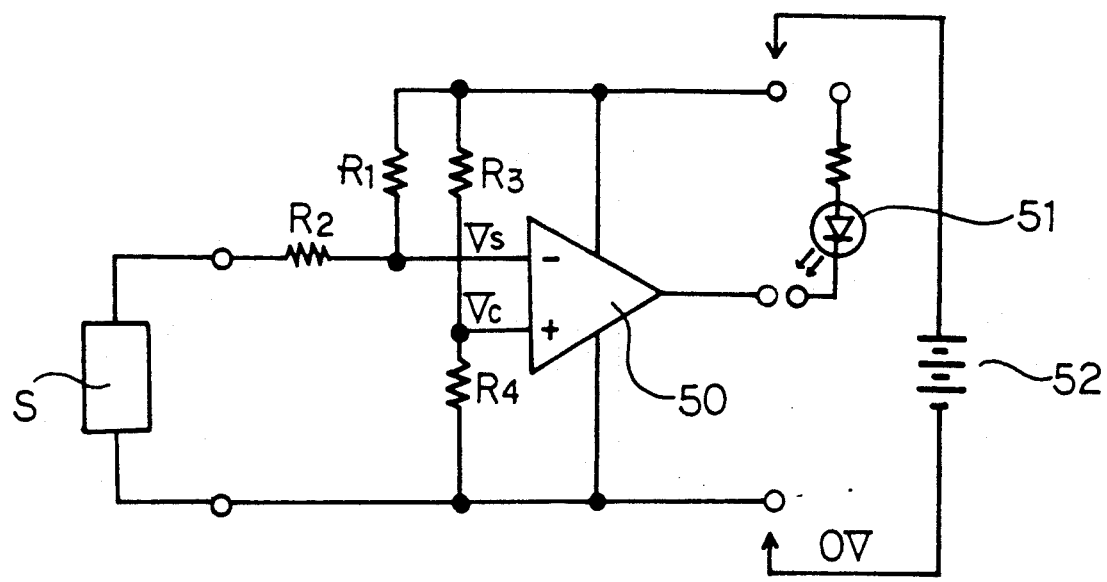
FIG. 5 is a simplified block diagram of the detection system according to an embodiment of the invention.

FIG. 5 designates the basic example of detection circuit of the detection system relates to the invention. As is clear from FIG. 5, the detection circuit comprises a sensor S, a comparator 50, an LED 51 serving as an alarm signal generator, and a regulated DC power supply source 52, which are respectively connected to each other via lead wires. Resistor R1 shown in the circuit diagram restricts current flowing into the sensor S. Resistor R2 protects input terminal of the comparator 50. Resistors R3 and R4 respectively set reference voltage of the comparator 50. As described earlier, normally, the detection circuit contains the reference voltage Vc which is higher than the measured terminal voltage Vs (Vs<Vc), and thus, no signal is output from the comparator 50.

However, as soon as the voltage value Vs exceeds or becomes even with reference voltage value Vc (Vs≧Vc), the comparator 50 outputs electric signal to light up the LED 51.

As a concrete example, when operating the sensor in a gasoline service station, as soon as the electric resistance value of the sensor exceeds 5 times the initial value, alarm signal is output. The circuit constants which can be used to generate an alarm signal are shown below. Assume that the initial value of the electric resistance $S_R$ of the sensor is 2 Kohm, voltage of the regulated DC power supply source is 5 V, resistance of the resistors $R_1$, $R_2$, $R_3$ and $R_4$ is respectively 50 Kohm, 3 Kohm, 50 Kohm and 13 Kohm. Based on these, the reference voltage Vc can be expressed by the equation shown below.

$$Vc = 5(V) \times \frac{R_4}{R_3 + R_4} \quad (1)$$

Based on the above equation (1), the reference voltage Vc is determined to be 1.03 V. On the other hand, normally measured terminal voltage Vs is expressed by the equation shown below.

$$Vs = 5(V) \times \frac{R_2 + S_R}{R_1 + R_2 + S_R} \quad (2)$$

Based on the above equation (2), the measured terminal voltage Vs calculated to be 0.455 V. Since Vc is higher than Vs, no signal are output from the comparator 50. When the resistance value of the sensor exceeds five times the initial value, in other words, when the resistance value of the sensor exceeds 10 Kohm, according to the equation (2) shown above, the measured terminal voltage Vs exceeds 1.03 V. This causes the relationship between both voltages to become Vc≦Vs. As a result, the comparator 50 outputs an alarm signal to light up the LED 51.

Next, circuit constants for generating an alarm signal when the resistance value of the sensor exceeds three times the initial value at a location without constantly handling gasoline is shown below. Assume that the initial resistance value of the sensor is 2 Kohm, voltage of the regulated DC power-supply source is 5 V, resistance values of the resistors $R_3$ and $R_4$ are respectively 50 Kohm and 9 Kohm. Based on these conditions, the reference voltage Vc becomes 0.763 V from the above equation (1), whereas the normally measured terminal voltage Vs becomes 0.455 V from the above equation (2). Since Vc is higher than Vs, no signal is output. Nevertheless, as soon as the resistance value of the sensor exceeds 6 Kohm which is three times the initial value, the measured terminal voltage Vs also exceeds 0.763 V from the above equation (2), thus realizing the relationship Vc≦Vs to allow the comparator 50 to output alarm signal.

Since the detection system according to the invention allows the operator to determine the reference voltage and the measured terminal voltage by properly setting the voltage of the power supply source, resistance values of resistors R1 through R4, and the initial resistance value of the sensor, the detection system can be installed to any location, thus offering extensive applicability.

The circuit shown in FIG. 5 merely represents an example. Needless to say that a variety of structures can also be materialized, for example, detection points can be increased by connecting a plurality of sensors in series.

THE FIRST THROUGH FOURTH EMBODIMENT AND THE FIRST AND SECOND COMPARATIVE EXAMPLES

Next, by referring to the first through fourth embodiments and the first and second comparative examples, the following description demonstrate the extremely sharp swelling property of the sensor of the invention, in other words, those embodiments demonstrate the extremely sharp responsiveness of the sensor by quickly increasing electric resistance in the presence of low molecular weight organic liquid and vaporized content.

taining 1% concentration of vaporized gasoline. Test results are shown in Table II that follows. Identical test conditions were applied to the invented and conventional sensors.

TABLE I

| | Upper stage: Thermoplastic elastomer Lower stage: Conductive carbon | Blend ratio (weight parts) | Shore A-hardness | Electric resistance (Kohm) | | | | |
|---|---|---|---|---|---|---|---|---|
| | | | | Initial value | 1 minute later | 2 minutes later | 3 minutes later | 5 minutes later |
| Embodiment No. 1 | SEBS *1 "KETZEN" BLACK | 100 25 | 52 | 10 | 40 | 100 | >5000 | — |
| Embodiment No. 2 | SEBS *1 "KETZEN" BLACK | 100 20 | 48 | 40 | 300 | >5000 | — | — |
| Embodiment No. 3 | Olefin elastomer *2 "KETZEN" BLACK | 100 15 | 60 | 10 | 18 | 27 | 50 | 1000 |
| Embodiment No. 4 | SEBS *1 "VULCAN" XC-72 | 100 80 | 65 | 20 | 50 | 150 | >5000 | — |
| Comparative example 1 | Cross-linked EP rubber "KETZEN" BLACK | 100 25 | 90 | 50 | 52 | 54 | 64 | 100 |
| Comparative example 2 | Cross-linked natural rubber "KETZEN" BLACK | 100 20 | 85 | 40 | 45 | 48 | 51 | 70 |

TABLE II

| | Upper stage: Thermoplastic elastomer Lower stage: Conductive carbon | Blend ratio (weight parts) | Shore A-hardness | Electric resistance (Kohm) | | | | |
|---|---|---|---|---|---|---|---|---|
| | | | | Initial value | 10 minutes later | 30 minutes later | 60 minutes later | 120 minutes later |
| Embodiment No. 1 | SEBS *1 "KETZEN" BLACK | 100 25 | 52 | 10 | 17 | 40 | 70 | 95 |
| Embodiment No. 2 | SEBS *1 "KETZEN" BLACK | 100 20 | 48 | 40 | 73 | 180 | 300 | 420 |
| Embodiment No. 3 | Olefin elastomer *2 "KETZEN" BLACK | 100 15 | 60 | 10 | 13 | 25 | 40 | 68 |
| Embodiment No. 4 | SEBS *1 "VULCAN" XC-72 | 100 80 | 65 | 20 | 32 | 70 | 125 | 180 |
| Comparative example 1 | Cross-linked EP rubber "KETZEN" BLACK | 100 25 | 90 | 50 | 50 | 52 | 55 | 60 |
| Comparative example 2 | Cross-linked natural rubber "KETZEN" BLACK | 100 20 | 85 | 40 | 40 | 40 | 42 | 45 |

*1: RABALON T-320C (MITSUBISHI PETROCHEMICAL CO., LTD.)
*2: MILASTOMER 5030 (MITSUI PETROCHEMICAL INDUSTRIES, LTD.)
Physical property:

| | specific gravity | melt flow rate |
|---|---|---|
| RABALON | 0.9 (JIS K7112) | 0.5 (g/10 minutes) (JIS K7210 at 230° C., 2.16 kg) |
| | density | melt flow rate |
| MILASTOMER | 0.88 (g/cm$^3$) (ASTM D1505) | 0.2 (g/10 minutes) (ASTM D1238 at 230° C., 2.16 kg) |

In order to embody the invention, the manufactured some number of sensors by producing conductive sheets having the shape shown in FIG. 1 from the combination of thermoplastic elastomer and conductive carbon (details are shown in Tables I an II that follow) which were not substantially cross-linked and had specific Shore A-hardness (see Tables I, II). Conventional sensors were used for comparative evaluation. Identical test conditions were applied to the invented and conventional sensors which respectively had conductive sheets each having 0.5 mm of thickness, 6.0 mm of width, and 50 mm of length.

THE FIRST EXPERIMENT

Inventors immersed one-side surface of the conductive sheets of the invented and conventional sensors in gasoline to measure variable electric resistance values based on timewise intervals. Test results are shown in Table I.

THE SECOND EXPERIMENT

Inventors measured variable electric resistance value based on timewise intervals after exposing sensors of the invention and conventional sensor to atmosphere con-

What is claimed is:

1. A sensor which detects presence of low molecular weight organic liquid or vapor thereof by sensing variation of electric resistance of a conductive sheet, wherein said conductive sheet comprises substantially non-cross-linked thermoplastic elastomer and conductive carbon, and Shore A-hardness of the sheet is a maximum of 70.

2. The sensor according to claim 1, wherein a region storing said conductive sheet and terminals connected thereto are disclosed in a water-proof structure.

3. The sensor according to claim 1, including a water-proof structure having a water-repellent film covering said conductive sheet.

4. The sensor according to claim 3, wherein said water-repellent film has a minimum of $10^4$ number of fine holes per square centimeter.

5. The sensor according to any of claim 1 wherein said conductive sheet and terminals connected thereto are covered with a reinforcing sheet and said reinforcing sheet is superficially covered with a water-repellent film.

6. The sensor according to any of claim 1 wherein a reinforcing layer is provided on the back of said conductive sheet having terminals connected thereto and a front surface thereof is covered with a water-repellent film.

7. The sensor according to claim 2, which is provided with water-proof structure includes a water-repellent film covering said conductor sheet.

8. The sensor according to claim 2, wherein said conductive sheet and terminals are covered with a reinforcing sheet and said reinforcing sheet is superficially covered with a water-repellent film.

9. The sensor according to claim 3, wherein said conductive sheet and terminals connected thereto are covered with a reinforcing sheet and said reinforcing sheet is superficially covered with said water-repellent film.

10. The sensor according to claim 4, wherein said conductive sheet and terminals connected thereto are covered with a reinforcing sheet and said reinforcing sheet is superficially covered with said water-repellent film.

11. The sensor according to claim 7, wherein said conductive sheet and terminals are covered with a reinforcing sheet and said reinforcing sheet is superficially covered with said water-repellent film.

12. The sensor according to claim 2, wherein a reinforcing layer is provided on a back of said conductive sheet and terminals, and a front surface thereof is covered with a water-repellent film.

13. The sensor according to claim 3, wherein a reinforcing layer is provided on a back of said conductive sheet and terminals connected thereto, and a front surface thereof is covered with said water-repellent film.

14. The sensor according to claim 4, wherein a reinforcing layer is provided on a back of said conductive sheet and terminals connected thereto, and a front surface thereof is covered with said water-repellent film.

15. The sensor according to claim 7, wherein a reinforcing layer is provided on a back of said conductive sheet and terminals, and a front surface thereof is covered with said water-repellent film.

16. The sensor according to claim 1, wherein said substantially non-cross-linked thermoplastic polymer is a styrene-ethylene-butadiene-styrene copolymer.

* * * * *